(12) United States Patent
Kaufman

(10) Patent No.: US 6,339,076 B1
(45) Date of Patent: *Jan. 15, 2002

(54) THERAPEUTIC FOOD COMPOSITION AND METHOD TO DIMINISH BLOOD SUGAR FLUCTUATIONS

(75) Inventor: Francine Kaufman, Los Angeles, CA (US)

(73) Assignee: Childrens Hospital Los Angeles, Los Angeles, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/129,052

(22) Filed: Aug. 4, 1998

Related U.S. Application Data

(63) Continuation of application No. 08/733,959, filed on Oct. 21, 1996, now Pat. No. 5,843,921, which is a continuation-in-part of application No. 08/418,210, filed on Apr. 7, 1995, now Pat. No. 5,605,893, which is a continuation-in-part of application No. 08/213,542, filed on Mar. 15, 1994, now abandoned.

(51) Int. Cl.[7] .......................................... A61K 31/715
(52) U.S. Cl. ..................... 514/60; 514/54; 514/866; 424/439; 424/441; 426/808
(58) Field of Search .................. 514/60, 54, 866; 426/808; 424/439, 441

(56) References Cited

U.S. PATENT DOCUMENTS

| | | | |
|---|---|---|---|
| 3,619,209 A | 11/1971 | Hegadorn et al. | 99/139 |
| 3,969,514 A | 7/1976 | Tiemstra | 426/90 |
| 4,496,606 A | 1/1985 | Michnowski | 426/658 |
| 4,629,725 A | 12/1986 | Hiji | 514/60 |
| 4,921,877 A | 5/1990 | Cashmere et al. | 514/866 |
| 5,097,023 A | 3/1992 | Ducep et al. | 536/17.4 |
| 5,169,662 A | 12/1992 | Spicer et al. | 426/449 |
| 5,232,733 A | 8/1993 | Resmer | 426/590 |
| 5,356,879 A | 10/1994 | Zehner et al. | 514/25 |
| 5,605,893 A | 2/1997 | Kaufman | 514/60 |
| 5,866,555 A * | 2/1999 | Bell et al. | 514/60 |
| 6,156,738 A | 12/2000 | Bell et al. | 514/60 |

FOREIGN PATENT DOCUMENTS

| | | | |
|---|---|---|---|
| EP | 0 443 789 | 8/1991 | |
| EP | 0 504 055 | 9/1992 | |
| EP | 0749697 A1 | 12/1996 | |
| WO | WO 95/24906 | 9/1995 | ......... A61K/31/715 |
| WO | WO 96/31129 | 10/1996 | ............. A23L/1/29 |

OTHER PUBLICATIONS

Goldberg et al.; "Nutrition therapy for hepatic glycogen storage diseases," *Journal of the American Dietetic Association* 93:12 1423–1430 (Dec. 1993).
Ogata et al., *Acta Paediatrica Japonica*, vol. 30, No. 5, pp. 547–522 (1988).
Boneh et al., *Am. J. Clin. Nutr.*, vol. 47, No. 6, pp. 1001–1003 (1988).
Kaufman et al., *J. Inv. Med.*, vol. 43, Supp. 1, p. 188A (1995).
Murphy, *Magazine of Children's Hospital of Los Angeles*, Winter 94/95, pp. 5–7.
Smit et al., *Pediatric Research*, vol. 18, No. 9, pp. 879–881 (1984).
Chen et al., *New England J. Medicine*, vol. 310, No. 3, pp. 171–174 (1984).
Behall et al., *Am. J. Clin. Nutr.*, vol. 47, pp. 428–432 (1988).
Hengesh, *Princ. Medicinal Chemistry*, (W. Foye 3rd ed.), pp. 531–550 (1989).
Wolfsdorf et al., *Am. J. Clin. Nutr.*, vol. 52, pp. 1051–1057 (1990).
Lozano et al., *Am. J. Clin. Nutr.*, vol. 52, pp. 667–670 (1990).
Glaser et al., *J. Pediatrics*, vol. 123, No. 4, pp. 644–650 (1993).
Wiesenfeld et al., *Proc. Soc. Exp. Biol. & Med.*, vol. 202, No. 3, pp. 338–344 (1993).
International Search Report on Corresponding PCT App. Serial No. PCT/US/95/10803 (1996).
Dawson, *Clin. Diabetes*, vol. 11, pp. 88–96 (1993).
Wolfsdorf et al., *Am. J. Clin. Nutr.*, vol. 56, pp. 587–592 (1992).
Simpson et al., *Am. J. Clin. Nutr.*, vol. 42, pp. 462–469 (1985).
Ververs et al., *European J. Clin. Nutr.*, vol. 47, No. 4, pp. 268–273 (1993).#jf139##

*Primary Examiner*—Kathleen Kahler Fonda
(74) *Attorney, Agent, or Firm*—Myers Bigel Sibley & Sajovec, P.A.

(57) ABSTRACT

A therapeutic food composition for treatment of diabetic patients to diminish fluctuations in blood sugar levels and prevent hypoglycemic episodes, comprising per unit about 20–50 grams of nutrients including slowly absorbed or digested complex carbohydrate, preferably uncooked cornstarch; more rapidly absorbed complex carbohydrate; protein; fat; and at least one sweetening agent, but less than about 3 grams of any simple sugar other than fructose. Fructose may be present in the composition in quantities greater than 3 grams per unit. Diabetic patients may be treated to diminish blood sugar fluctuations and prevent hypoglycemia via the administration of the novel food composition as an evening or pre-bedtime snack-or during the daytime hours to patients receiving insulin therapy or engaging in activities that might provoke hypoglycemia.

61 Claims, 1 Drawing Sheet

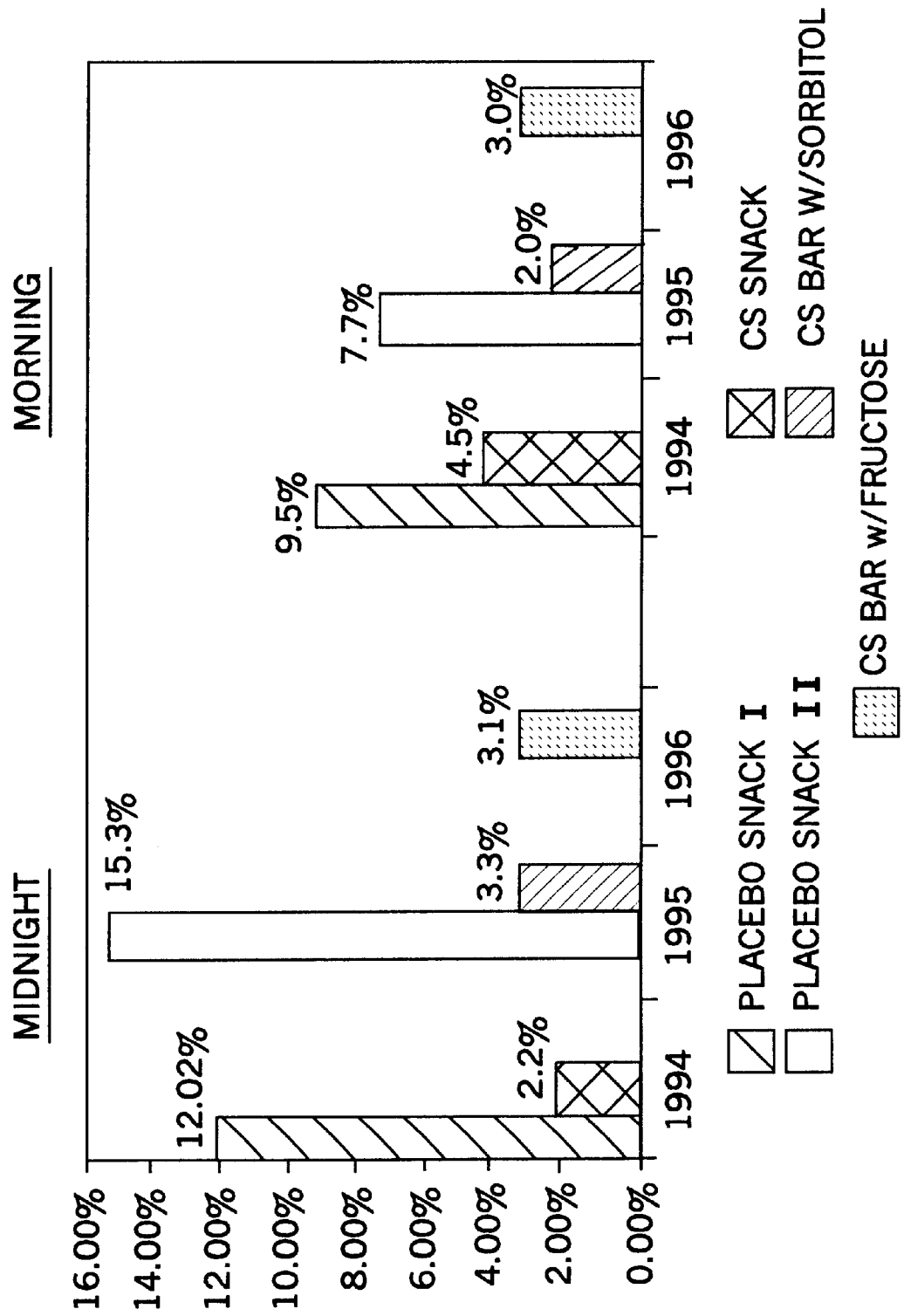

THERAPEUTIC FOOD COMPOSITION AND METHOD TO DIMINISH BLOOD SUGAR FLUCTUATIONS

CROSS-REFERENCE TO RELATED APPLICATIONS

This application is a continuation of U.S. application Ser. No. 08/733,959, filed Oct. 21, 1996, now U.S. Pat. No. 5,843,921, which is a continuation-in-part of application Ser. No. 08/418,210, filed Apr. 7, 1995, U.S. Pat. No. 5,605,893, which is a continuation-in-part of application Ser. No. 08/213,542, filed Mar. 15, 1994, now abandoned.

BACKGROUND OF THE INVENTION

1. Field of the Invention

This invention relates to therapeutic treatments of diabetes mellitus. More particularly, this invention relates to treatment methods and compositions for the prevention of severe fluctuations in blood sugar levels in diabetic patients.

2. Description of the Prior Art

Symptoms of hypoglycemia fall into two main categories. Rapid epinephrine release causes sweating, tremor, tachycardia, anxiety, and hunger. Central nervous system symptoms include dizziness, headache, clouding of vision, blunted mental acuity, confusion, abnormal behavior, convulsions and loss of consciousness. When hypoglycemia is recurrent or severe, nervous system symptoms predominate, and the epinephrine phase may not be recognizable. With more rapid drops or wide swings in plasma glucose (as in insulin reactions), adrenergic symptoms are prominent (*Harrison's Principles of Internal Medicine*, 11th Ed., McGraw-Hill Book Company, New York, 1987, p. 1800).

Numerous strategies have been developed to achieve the goal of maintaining blood glucose at a relatively constant level in diabetic patients, such as open looped continuous subcutaneous insulin pumps and multiple daily injections of insulin. These intensive insulin regimens are coupled with home glucose monitoring, and many patients measure their blood glucose levels by finger prick up to 6 to 8 times per day to assure that close to normal blood sugar levels are maintained. This regimen is prescribed because studies have shown that by avoiding excessive high blood sugar levels, the long-term outcome of patients with diabetes can be improved. However, this regimen, which decreases episodes of high blood sugar, also causes patients to experience more low blood sugar reactions (hypoglycemia).

Results of the Diabetes Complication and Control Trial indicate that intensive insulin treatment, while it markedly delays and lessens long term retinal, nephrologic and neuropathic disease, leads to a three to nine-fold increase in hypoglycemic events, most of which occur at night (L. Y. Dawson, *Clinical Diabetes*, 11:88–96, 1993). Sometimes these episodes of hypoglycemia are severe and can lead to loss of consciousness and convulsions. Severe hypoglycemic events seem to occur more often at night while the patient is asleep rather than during the day. When awake, diabetic patients can feel hypoglycemic reactions beginning, and can treat themselves with sugar in order to bring their blood sugar levels back into the normal range. When asleep, patients do not have this awareness, and therefore the risk of hypoglycemia is much higher during this time.

The need exists to develop strategies to diminish hypoglycemia while continuing to intensively manage diabetes. Cornstarch has been used effectively to combat the hypoglycemia associated with glycogen storage disease type 1, a disease having an inherited absence or deficiency of glucose-6-phosphatase activity in the liver, kidneys, and intestines, leading to accumulation of glycogen in those organs and hypoglycemia during fasting. Protection against low blood sugar was provided for up to 6 to 8 hours after ingestion of uncooked cornstarch (J. I. Wolfsdorf, et al., *Am. J. Clin. Nutr.*, 51:1051–7, 1990). However, the dosage of cornstarch used for this treatment was 1.75 grams per kilogram of body weight. This dosage is much higher than could be tolerated by a patient with diabetes mellitus.

Another study has also been conducted in patients with diabetes, giving cornstarch during inpatient hospitalization, with a reduction in the nadir of the blood glucose level. Children were fasted and then given the entire carbohydrate content of the standard bedtime snack (30 grams of carbohydrate) as uncooked cornstarch (M. T. Ververs, et al., *Eur. J. Clin. Nutr.*, 47:268–73, 1983). However, in this study the cornstarch did little to prevent hypoglycemia and the researchers did not evaluate varying dosages to determine maximal efficacy.

Thus, the need exists for a better method of treating hypoglycemia in both Type I and Type II diabetics. In particular, a method of treatment or maintenance is required which will avoid serious hypoglycemic episodes while not provoking hyperglycemia.

SUMMARY OF THE INVENTION

Blood glucose levels in patients with diabetes mellitus are regulated and stabilized by administering to the patients a therapeutic food composition including a slowly metabolized complex carbohydrate, preferably uncooked cornstarch; a more rapidly metabolized complex carbohydrate; protein; fat; and fructose or non-sugar sweeteners (e.g., sugar alcohols or artificial sweeteners). The composition is preferably substantially free of simple sugars, but may contain a small quantity (up to 3 grams per unit) of sugars such as sucrose. The composition is slowly absorbed from the gastrointestinal tract and maintains relatively stable blood sugar levels in the diabetic patient for up to nine hours without having any significant adverse effects on the digestive system.

The therapeutic food composition, which may be in the form of a snack bar, is preferably administered to diabetic patients shortly before bedtime, and is effective in substantially preventing nocturnal episodes of hypoglycemia while not causing hyperglycemia.

BRIEF DESCRIPTION OF THE DRAWINGS

FIG. 1 is a bar graph reflecting the percentage incidence of hypoglycemia in diabetic patients whose blood glucose levels were measured at midnight and in the morning during studies conducted in 1994, 1995 and 1996, respectively, the patients having received bedtime snacks as indicated.

DETAILED DESCRIPTION OF THE INVENTION

The present invention pertains to a therapeutic food composition intended for administration to patients suffering from Type I or Type II diabetes to help maintain proper blood glucose regulation and prevent wide fluctuations therein, namely, hypoglycemic and hyperglycemic episodes. The therapeutic composition is to be administered as part of an overall program of treatment, including control of diet and the administration of insulin and/or other medications in appropriate cases.

The novel food composition comprises as its essential components:
  a) a complex carbohydrate which is slowly absorbed from the human gastrointestinal tract (hereinafter "slowly absorbed carbohydrate"), i.e., is slowly digested and is not completely metabolized even after 34 hours;
  b) a complex carbohydrate which is more rapidly absorbed from the digestive tract (hereinafter "rapidly absorbed carbohydrate");
  c) protein;
  d) fat; and
  e) at least one sweetening agent.

As used herein, the term "complex carbohydrates" refers to macromolecular carbohydrates including starches, polydextrose and other polysaccharides. The term "sweetening agent" refers to simple sugars (e.g., sucrose, lactose, galactose and fructose), sugar alcohols used as sweeteners (e.g., sorbitol or maltitol) and artificial sweeteners (e.g., aspartame and sodium saccharin); however, as discussed below, the composition may not contain more than about 3 grams of any simple sugar other than fructose.

The therapeutic composition containing the foregoing components may be in any conventional "snack" form, e.g., bars, puddings, cookies, wafers, milkshakes and the like. Snack-type bars resembling candy or granola bars are most convenient for storage, handling and administration purposes and, when produced with scores, perforations or grooves thereon, can be easily divided for purposes of administering a fraction of a bar where appropriate.

The novel food composition preferably contains about 20 to about 50 grams of nutrients per serving or unit, e.g., per bar, including:
  about 15–35 grams of total carbohydrates (about 5–15 grams of slowly absorbed complex carbohydrate, about 7–20 grams of rapidly absorbed complex carbohydrate and about 0–15 grams of a simple sugar, a sugar alcohol, or a combination thereof, provided that no more than about 3 grams of simple sugars other than fructose are included;
  about 3–20 grams of protein; and
  about 2–7 grams of fat.

The composition may also contain non-nutritive artificial sweeteners such as aspartame, sodium saccharin and acesulfame potassium.

The term "nutrients" as used herein refers to carbohydrates, proteins and fats.

The therapeutic food composition of the invention preferably provides about 100–230 calories per serving or unit, of which:
  about 50–75% are from slowly absorbed and rapidly absorbed complex carbohydrates;
  about 10–25% are from protein; and
  about 10–25% are from fat.

In a preferred embodiment of the invention, the novel food composition is in the form of a bar including 17–25 grams of total carbohydrate, or the equivalent of one to one and one-half "bread exchanges" in a standard diabetic diet plan. The bar contains about 5–15 grams of slowly absorbed carbohydrate in the form of uncooked cornstarch, which generally comprises by weight about 27% amylose and 73% amylopectin. The preferred embodiment also contains about 7–20 grams of rapidly absorbed complex carbohydrate including about 3–15 grams of fructose, sorbitol, maltitol or a combination thereof and 0–3 grams of simple sugars other than fructose; about 3–12 grams of protein; and about 2–7 grams of fat.

Fructose (also known as D-fructose and levulose) is a simple sugar, $C_6H_{12}O_6$, with a molecular weight of about 180 found in a large number of fruits and in honey. It occurs in both the furanose and pyranose forms.

Sorbitol (also known as D-sorbitol and D-glucitol) is a hexahydric alcohol, $C_6H_8(OH)_6$, with a molecular weight of about 182 found in berries, cherries, plums and other fruits and in seaweed. It is about 60% as sweet as sucrose (on a weight/weight basis).

It has been established in the scientific literature that fructose is metabolized or converted to glycogen even in the absence of insulin; hence, fructose may be used at least in moderate levels as a sweetener in food products intended for consumption by patients suffering from Type I (insulin-dependent) diabetes without serious consequences. Similarly, about 70% of orally ingested sorbitol is converted to $CO_2$ without appearing as glucose in the blood. Sorbitol, however, is known to cause digestive problems in some individuals following consumption, including cramps and gas pains. Any such untoward side effects of consuming the therapeutic food composition will decrease patient compliance with a regimen that requires consuming such compositions on a regular basis, e.g., as a bedtime snack. Hence, in the case of diabetic patients sensitive to sorbitol it is desirable to administer a food composition which contains uncooked cornstarch and the other components disclosed herein, has a sweet and palatable taste and texture, does not contain substantial quantities of sugars which impact adversely on the maintenance of normal blood sugar levels and does not cause digestive upset.

It has been discovered that replacement of the sorbitol by fructose in the cornstarch-containing food composition disclosed in U.S. Pat. No. 5,605,893, yields a composition as effective in controlling blood sugar fluctuations and hypoglycemic episodes in diabetics, but without the adverse digestive symptoms frequently caused by sorbitol and certain artificial sweeteners.

The ingredients in the subject food composition may include any conventional food ingredients of adequate purity and wholesomeness which preferably supply the aforementioned amounts of total calories and percentage of calories from carbohydrates, protein and fat, respectively, and wherein the relative weight ranges of slowly absorbed carbohydrates, rapidly absorbed carbohydrates, protein, fat and fructose are as indicated previously. In the preferred embodiment of a snack-type bar, the ingredients may include, by way of illustration, uncooked cornstarch as the slowly absorbed carbohydrate; polydextrose, peanuts, peanut derivatives (e.g., peanut butter), other nuts or nut derivatives as sources of rapidly absorbed carbohydrates, fat and protein; and other protein sources such as soy protein, whey protein, and casein hydrolysate. Artificial sweeteners (e.g., aspartame or saccharin) may be included in the food composition in small amounts, but fructose and/or sorbitol and maltitol (3–15 grams) are the principal sweeteners. Coloring agents, water, salt, preservatives and other standard ingredients or additives normally used in the preparation of a snack or candy-type bar may be utilized, as well as up to 3 grams of simple sugars other than fructose (e.g., sucrose, lactose or galactose), provided that the total nutrient and calorie profile of the finished bar or other form of the novel food composition comes within the parameters defined above.

Uncooked cornstarch is the preferred source of slowly absorbed carbohydrate for purposes of the invention since its carbohydrate content and its rate of metabolism are known and are relatively uniform, and it may be readily formulated into a variety of palatable food compositions.

Many diabetics routinely consume a bedtime snack containing about 30 grams of carbohydrate, often in the form of bread, cereal or milk. By the method of treatment of the present invention, patients suffering from diabetes mellitus are administered in place of, or as part of, their normal evening or pre-bedtime snack (in accordance with their recommended bread and protein exchanges) one to two servings or units of the therapeutic food composition, for example one to two bars prepared in accordance with the invention. The number of units administered, including fractions of a unit (such as half bars), will depend on the age, weight and condition of the patient, whether or not the patient takes insulin or other antidiabetic medication and the patient's nocturnal blood sugar profile as determined by finger stick blood glucose levels or other means of blood sugar management. The goal of the treatment is to prevent blood glucose levels from dropping below 60 mg/dl, defined as hypoglycemia, while not rising above 250 mg/dl, defined as hyperglycemia.

Dosage amounts of less than one unit may be utilized in younger pediatric patients or in patients who have demonstrated relatively little tendency towards nocturnal hypoglycemic events.

It has been found in clinical studies with diabetic children and adolescents that food compositions prepared in accordance with the invention and administered as described herein are effective in maintaining blood sugar levels in the "normal" range of 60–250 mg/dl for as long as 8–9 hours or more after ingestion.

Patients taking insulin can also be treated during the day with premeasured doses of the novel food composition, which will be slowly metabolized to the monosaccharide glucose over a period of six to eight hours, instead of receiving primarily simple carbohydrates such as are contained in orange juice or other sugar sources that tend to cause a rapid peak in blood glucose level which subsides quickly.

During waking hours the patient's use of, and hence requirement for, glucose is varied and depends upon the level and type of activity, e.g., vigorous exercise. The exact amount and frequency of the actual dose, therefore, will vary by patient and from day to day for each patient. A blood glucose test, usually administered as a finger stick to obtain a blood sample, can be used to monitor daily glucose levels as well as the patient's own subjective experience of symptoms associated with the onset of hypoglycemia. Therefore, in the practice of this invention sufficient complex carbohydrate is administered in the form of the novel food composition to maintain the blood glucose level somewhat above this level, nominally about 60 mg/dl in the average patient.

It will be appreciated by persons of skill in the medical arts generally and in the management of diabetic patients specifically that the composition and method of the present invention are valuable adjuncts to conventional diet management and drug or insulin therapy and can provide an easily administered and accepted modality to avoid excessive peaks and valleys in blood glucose levels, particularly the severe hypoglycemic episodes which are experienced by many diabetics.

The following are illustrative examples of the novel composition and method of the present invention. These examples are not intended, however, to provide ingredients, specific formulations, methods of production or dosage regimens which must be utilized exclusively to practice the invention.

EXAMPLE 1

Bar Containing Cornstarch and Sorbitol

A therapeutic food composition was prepared in accordance with the invention in the form of a snack-type vanilla nut bar. The bar weighed a total of 31 g and contained cornstarch, sorbitol, soy protein isolate, peanut butter, water, polydextrose, peanuts, whey protein concentrate, natural flavors, lecithin and citric acid.

Nutritionally, the bar provided 120 calories and was equivalent to one and one-half bread exchanges. About 57% of the calories were from carbohydrates, 23% from protein and 20% from fat. The bar included 7 g of protein and about 2.5 g of total fat: about 0.5 g saturated fat, 1 g polyunsaturated fat and 1 g monounsaturated fat.

The total carbohydrate content of the bar was 17 g, of which 5 g were cornstarch (uncooked) and about 12 g were more rapidly absorbed simple and complex carbohydrates, including sugar alcohols (sorbitol and maltitol) and the carbohydrates in the polydextrose and peanuts.

EXAMPLE 2

Materials and Methods

This study was performed to compare the cornstarch-containing snack bar of Example 1 with a placebo snack bar of equal carbohydrate, protein, fat and caloric content in terms of their effects on blood glucose levels in diabetic patients. The bar of Example 1 is referred to herein as "bar 1" while a placebo bar containing the same number of grams of carbohydrates but no cornstarch is referred to as "bar 2".

The study was conducted during the 1995 teen session at the American Diabetes Association sponsored Camp Chinnock, in Southern California. Seventy-nine of a potential 115 campers and counselors entered this study after they were solicited with a letter describing the study protocol, and after they and/or their parents signed an informed consent.

The subjects were 14–30 years of age, there were 33 males and 46 females, with a duration of diabetes from 1.5 to 19 years. Half of the subjects were on two injections per day, while the remainder were on three or more, or used continuous subcutaneous insulin infusion. Glycated hemoglobin levels were reported on the camp form in 73 study subjects. Levels were analyzed by percent above the upper limit of the reported assay norm, and divided into quartiles.

Thirty-nine subjects were randomly assigned to receive bar 1 for 5 nights, followed by bar 2 for 5 nights (Group A), while forty subjects were randomly assigned to receive the bars in the opposite order (Group B). Snack bars were eaten with 4 oz. of milk as the evening snack if the blood glucose level was $\geq 120$ mg/dl. In addition to the bars, if the blood glucose level was $\geq 80$ and <120 mg/dl, ½ starch and ½ protein exchanges were added; if the blood glucose was $\geq 50$ and <80 mg/d., 1 fruit exchange was added to the ½ starch and ½ protein exchanges, and if the blood glucose level was <50 mg/dl, 1½ fruit exchanges were given in addition to the ½ starch and ½ protein exchanges. The campers, counselors, staff, dieticians, and physicians deciding the insulin dosages and treatments for hypoglycemia were blind to the snack bar assignment. Only the research assistants knew which campers had consumed which bars, but they had no other role in diabetes management.

The goal of the medical management was to maintain the subjects' blood glucose levels in the targeted range of 70–150 mg/dl, avoiding extremes of glycemic excursion. On the first day of camp, the home insulin dosage was decreased by 15%. Thereafter, insulin dosage adjustment was done daily by the medical staff under the supervision of a pediatric endocrinologist.

Participants ate 3 full meals and 3 snacks per day composed of 25% fat, 50% carbohydrate and 25% protein, and subjects were encouraged to consume their usual caloric intake. The evening snack was given between 21:00 to 21:30 nightly. Carbohydrate intake after each meal was recorded by the staff dieticians as reported by campers. All subjects routinely tested their blood glucose levels with a glucose meter (One Touch, Lifescan, Inc., Milpitas, Calif. or Glucometer Elite, Miles Inc., Elkhart, Ind.) 5 times per day: before breakfast, lunch, dinner, evening snack and between midnight and 0100. Glucose meters were checked for accuracy with high and low standards daily by nursing staff. Subjects participated in the full range of camping activities without restrictions. Hypoglycemia was treated according to a standard protocol.

Comparisons of the number of hypoglycemic events, defined as a blood glucose level <60 mg/dl, and the number of hyperglycemic events, defined as a blood glucose levels >250 mg/dl, occurring at midnight and at 0700, were made for the cornstarch bar nights versus the control bar nights. In addition, comparisons were made for snack bar 1 and snack bar 2 for Group A and Group B. Statistical analysis to compare blood glucose levels was done with the Fisher's Exact test. McNemar's test was used to compare blood glucose levels for individual campers and chi square was used for glycated hemoglobin.

Results

There was a significant difference in the number of hypoglycemic events at midnight between bar 1 and bar 2 for the total cohort and for Groups A and B (Table 1). A similar result occurred in the morning for the total cohort and Group A; however, statistical significance was not reached for Group B. As shown in Table 2, there was a significant decrease in the number of hyperglycemic events for the total cohort at midnight when bar 1 was ingested compared to bar 2. There was a significant decrease in the number of subjects to ever experience a hypoglycemic event at both midnight and in the morning when bar 1 was taken compared to bar 2 (Table 3).

Conclusion

The data suggests that in subjects with diabetes the cornstarch bar can diminish the incidence of hypoglycemia and reduce the number of subjects experiencing hypoglycemia at midnight, 3–4 hours after ingestion, and in the morning, 9–10 hours after ingestion. This decrease in hypoglycemia was not accompanied by a concurrent increase in hyperglycemia at these time periods. The improvement in glycemia appears to be due to the difference in the composition of the snack bars themselves, and not due to anything else that could have affected blood glucose control during this study, such as the carbohydrate intake at dinner or the overall insulin dosages administered.

TABLE 1

NUMBER (%) OF HYPOGLYCEMIC EVENTS

| | Midnight | | | Morning | | |
|---|---|---|---|---|---|---|
| | Group A | Group B | Total Bar 1 | Group A | Group B | Total Bar 1 |
| Bar 1 | 7/194 (3.6%) | 6/199 (3/0%) | 13/393 (3.3%) | 2/195 (1.0%) | 6/199 (3.0%) | 8/394 (2.0%) |
| | Group B | | Total Bar 2 | Group B | | Total Bar 2 |
| Bar2 | 40/198 (20.2%) | 19/189 (10.1%) | 59/387 (15.3%) | 15/199 (7.5%) | 15/191 (7.9%) | 30/390 (7.7%) |
| | Group A p = 0.014 | Group B p < 0.001 | Total p < 0.001 | Group A p = 0.001 | Group B p = 0.072 | Total p = 0.001 |

TABLE 2

NUMBER (%) OF HYPOGLYCEMIC EVENTS

| | Midnight | | | Morning | | |
|---|---|---|---|---|---|---|
| | Group A | Group B | Total Bar 1 | Group A | Group B | Total Bar 1 |
| Bar 1 | 12/194 (6.2%) | 13/199 (6.5%) | 25/393 (6.4%) | 7/195 (3.6%) | 13/199 (6.5%) | 20/294 (5.1%) |
| | Group B | | Total Bar 2 | Group B | | Total Bar 2 |
| Bar2 | 23/198 (11.6%) | 20/198 (10.6%) | 43/387 (11.1%) | 18/199 (9.1%) | 14/191 (7.3%) | 32/390 (8.2%) |
| | Group A p = 0.041 | Group B p < 0.083 | Total p < 0.022 | Group A p = 0.120 | Group B p = 0.455 | Total p = 0.086 |

TABLE 3

NUMBER (%) OF CAMPERS TO
EVER EXPERIENCE HYPOGLYCEMIA

|  | Midnight |  | Morning |  |
| --- | --- | --- | --- | --- |
| Bar 1 | 12/79 | (15.2%) | 7/79 | (8.9%) |
| Bar 2 | 41/79 | (52.9%) | 23/79 | (29.1%) |
|  | $p < 0.001$ |  | $p = 0.002$ |  |

EXAMPLE 3

Bar Containing Cornstarch and Fructose

A therapeutic food composition was prepared in accordance with the invention in the form of a snack-type chocolate crunch bar. The bar weighed a total of 33 g and contained cornstarch, fructose, soy protein isolate, maltitol syrup, crisp rice (rice flour, malt extract, rice bran), polydextrose, cocoa, non-fat milk, glycerine, canola oil, natural flavors, gum arabic and lecithin.

Nutritionally, the bar provided 120 calories (equivalent to one bread exchange), of which about 64% were from carbohydrates, 17% from protein and 19% from fat. The bar included 5 g of protein and about 2.5 g of total fat.

The total carbohydrate content of the bar was 22 g, of which 5 g were cornstarch (uncooked) and about 17 g were more rapidly absorbed carbohydrate, including 6 grams of fructose, 3 grams of maltitol and the remainder provided primarily by the polydextrose and peanuts.

The bar contained 90 mg of sodium and 90 mg of potassium.

EXAMPLE 4

In the summer of 1996 (July 30 through August 10), a further study was conducted at Camp Chinnock in Southern California. This study was approved by the Committee on Clinical Investigations at Children Hospital Los Angeles and informed consent was obtained from the subjects and/or their parents prior to entry.

The study involved 32 campers and counselors with Type I diabetes. Subjects were given the fructose-containing bar of Example 3 as the evening snack with 4 oz. of non-fat milk (unless the blood glucose level was <120 mg/dl at which time added carbohydrate and protein were included per a set algorithm). Results were compared to the established incidence of hypoglycemia and hyperglycemia (blood glucose level <60 mg/dl or >250 mg/dl) as defined in the study from the summer of 1995 described in Example 2. The results were also compared with the results of a study conducted in 1994 wherein two groups of diabetic patients were given either a standard nighttime snack or uncooked cornstarch in sugar-free pudding or milk (this study was reported in Kaufman, et al., *Diabetes Res. Clin. Prac.*, 30: 205–209, 1995). The incidence of hypoglycemia was further compared to that seen in 1995 with the uncooked cornstarch bar of Example 1, containing sorbitol but no fructose.

With the ingestion of the fructose-containing cornstarch snack bar the incidence of hypoglycemia for the 5 nights of the study in these subjects was 3.1% at midnight; the incidence of hyperglycemia at midnight was 10.3% (compared to 1994 incidence with the non-cornstarch snack (Placebo I) of hypoglycemia at midnight of 12.2%, p<0.001 and a 1995 incidence with the placebo snack (Placebo II) of 15.3%, p<0.001, and a hyperglycemia incidence of 11.1%, p=NS). The incidence of hyperglycemia in the morning was 3.0%; the incidence of hyperglycemia in the morning was 9.3% (compared to 1994 incidence of hypoglycemia in the morning of 9.5%, p<0.05 and a 1995 incidence of 7.7%, p<0.01, and a hyperglycemia incidence of 8.2%, p=NS).

Comparisons of data generated by the studies conducted in 1994, 1995 (Example 2) and 1996 (Example 4) are shown in graphic form in FIG. 1.

TABLE 4

COMPARISON OF HYPOGLYCEMIC EPISODES
WITH FRUCTOSE-CORNSTARCH BAR VS.
SORBITOL CORNSTARCH BAR

|  | MIDNIGHT | MORNING |
| --- | --- | --- |
| Fructose Bar (Incidence of hypoglycemia) | 3.1% | 3.0% |
| Sorbitol Bar (Incidence of hypoglycemia) | 3.3% | 2.0% |

As reflected in Table 4, there was no significant difference in the incidence of hypoglycemia at midnight and in the morning with the fructose-containing bar versus the sorbitol-containing bar.

EXAMPLE 5

The fructose-containing bar of Example 3 was compared with the sorbitol containing bar of Example 1 in four normal subjects. The subjects were given 3¾ snack bars containing the uncooked cornstarch with fructose formulation and the results were compared to the sorbitol-cornstarch bar formulation. The insulin, blood glucose and glucagon responses to the fructose bars were similar to what had been seen with the sorbitol formulation and distinctly different than the responses observed with the placebo bar. These data suggest that the delayed absorption of the carbohydrate in the uncooked cornstarch formulation was identical when fructose was used to replace some of the sorbitol in the original formula to enhance flavor and avoid digestive upset.

The unique formulation of the novel food composition, blending slowly and rapidly absorbed carbohydrates, protein and fat, allows for the gradual hydrolysis and absorption of the complex carbohydrates and maintains the blood sugar level stable for up to eight to nine hours, diminishing hypoglycemia in diabetic subjects after the post prandial period.

Whether the sorbitol or fructose-containing form of the novel composition is administered to particular patients is within the sound discretion of the medical practitioner. If a patient experiences digestive upset or other gastrointestinal symptoms after consuming the sorbitol-containing preparation, or if the patient dislikes the taste of that composition, it would be wise to switch that patient to the fructose-containing composition. Of course, sweeteners other than fructose and sorbitol may also be included in the therapeutic food composition without departing from the scope of this invention, provided that each unit of the composition contains no more than 3 grams of simple sugars other than fructose.

It has thus been shown that there are provided compositions and methods which achieve the various objects of the invention and which are well adapted to meet the conditions of practical use.

As various embodiments might be made of the above invention, and as various changes might be made in the embodiments set forth above, it is to be understood that all matters herein described are to be interpreted as merely illustrative.

What is claimed as new and desired to be protected by letters patent is set forth in the following claims:

I claim:

1. A method of treating a diabetic patient to decrease hypoglycemic episodes, the method comprising administering to the patient a therapeutic food composition comprising per serving or unit about 20–50 grams of nutrients including about 5–15 g of uncooked cornstarch wherein no more than about 3 g of simple sugars other than fructose are included.

2. The method according to claim 1, wherein the composition comprises per serving or unit about 15–35 g of total carbohydrates.

3. The method according to claim 1, wherein the composition contains about 5 g of cornstarch per serving or unit.

4. The method according to claim 1, wherein the composition comprises at least one sweetening agent selected from the group consisting of fructose, sugar alcohols, artificial sweetener, and combinations thereof.

5. The method according to claim 1, wherein the composition comprises at least one sweetening agent selected from the group consisting of fructose, sugar alcohols, aspartame, sodium saccharin, and acesulfame, and combinations thereof.

6. The method according to claim 1, wherein the composition comprises a rapidly absorbed complex carbohydrate.

7. The method according to claim 6, wherein the composition comprises about 7–20 g of a rapidly absorbed complex carbohydrate per serving or unit.

8. The method according to claim 1, wherein the composition comprises about 0–15 g per serving or unit of simple sugars, sugar alcohols, or a combination thereof.

9. The method according to claim 1, wherein the composition comprises about 3–15 g per serving or unit of fructose, sugar alcohols, or a combination thereof.

10. The method according to claim 1, wherein the composition comprises about 3–15 g of fructose per serving or unit.

11. The method according to claim 1, wherein the composition comprises about 6 g of fructose per serving or unit.

12. The method according to claim 1, wherein the composition comprises per serving or unit about 3–15 g of sugar alcohols selected from the group consisting of sorbitol, maltitol and a combination thereof.

13. The method according to claim 1, wherein the composition comprises sorbitol.

14. The method according to claim 1, wherein the composition comprises a simple sugar selected from the group consisting of sucrose, lactose and galactose.

15. The method according to claim 1, wherein the composition is substantially free of simple sugars.

16. The method according to claim 1, wherein the composition comprises about 3–20 g of protein per serving or unit.

17. The method according to claim 1, wherein the composition comprises about 2–7 g of fat per serving or unit.

18. The method according to claim 17, wherein about one-third of the fat is monounsaturated.

19. The method according to claim 1, wherein the composition is in the form of a snack bar, pudding, cookie, wafer, or milkshake.

20. The method according to claim 1, wherein the composition is in the form of a snack bar.

21. The method according to claim 20, wherein the snack bar is produced with scores, perforations or grooves thereon for division into fractions of a unit.

22. The method according to claim 1, wherein about 1–2 servings or units of the composition are administered to the patient.

23. The method according to claim 1, wherein about one-half serving or unit of the composition are administered to the patient.

24. The method according to claim 1, wherein the composition is administered to the patient as an evening or pre-bedtime snack.

25. The method according to claim 1, wherein the composition is administered during the daytime to a patient receiving insulin therapy or engaging in exercise.

26. The method according to claim 1, wherein the patient is a child or adolescent.

27. The method according to claim 1, wherein the patient has Type I diabetes.

28. The method according to claim 1, wherein the patient has Type II diabetes.

29. A method of treating a diabetic patient to diminish fluctuations in blood sugar levels, the method comprising administering to the patient a therapeutic food composition comprising per serving or unit about 20–50 grams of nutrients including about 5–15 g of uncooked cornstarch wherein no more than about 3 g of simple sugars other than fructose are included.

30. A method of treating a diabetic patient to decrease nighttime hypoglycemic episodes, the method comprising administering to the patient a therapeutic food composition comprising per serving or unit about 20–50 grams of nutrients including about 5–15 g of uncooked cornstarch wherein no more than about 3 g of simple sugars other than fructose are included.

31. The method according to claim 30, wherein the composition is administered to the patient as an evening or pre-bedtime snack.

32. The method according to claim 30, wherein the patient is a child or adolescent.

33. The method according to claim 30, wherein the patient has Type I diabetes.

34. The method according to claim 30, wherein the patient has Type II diabetes.

35. The method according to claim 29, wherein the composition comprises per serving or unit about 15–35 g of total carbohydrates.

36. The method according to claim 29, wherein the composition contains about 5 g of cornstarch per serving or unit.

37. The method according to claim 29, wherein the composition comprises at least one sweetening agent selected from the group consisting of fructose, sugar alcohols, artificial sweetener, and combinations thereof.

38. The method according to claim 29, wherein the composition comprises a rapidly absorbed complex carbohydrate.

39. The method according to claim 29, wherein the composition comprises about 0–15 g per serving or unit of simple sugars, sugar alcohols, or a combination thereof, wherein no more than about 3 g of simple sugars other than fructose are included.

40. The method according to claim 29, wherein the composition comprises less than about 3 g of simple sugars other than fructose per serving or unit.

41. The method according to claim 29, wherein the composition comprises a simple sugar selected from the group consisting of sucrose, lactose and galactose.

42. The method according to claim 29, wherein the composition is substantially free of simple sugars.

43. The method according to claim 29, wherein the composition comprises about 3–20 g of protein per serving or unit.

44. The method according to claim 29, wherein the composition comprises about 2–7 g of fat per serving or unit.

45. The method according to claim 29, wherein the composition is in the form of a snack bar, pudding, cookie, wafer, or milkshake.

46. The method according to claim 29, wherein about 1–2 servings or units of the composition are administered to the patient.

47. The method according to claim 29, wherein about one-half serving or unit of the composition are administered to the patient.

48. The method according to claim 29, wherein the composition is administered during the daytime to a patient receiving insulin therapy or engaging in exercise.

49. The method according to claim 30, wherein the composition comprises per serving or unit about 15–35 g of total carbohydrates.

50. The method according to claim 30, wherein the composition contains about 5 g of cornstarch per serving or unit.

51. The method according to claim 30, wherein the composition comprises at least one sweetening agent selected from the group consisting of fructose, sugar alcohols, artificial sweetener, and combinations thereof.

52. The method according to claim 30, wherein the composition comprises a rapidly absorbed complex carbohydrate.

53. The method according to claim 30, wherein the composition comprises about 0–15 g per serving or unit of simple sugars, sugar alcohols, or a combination thereof, wherein no more than about 3 g of simple sugars other than fructose are included.

54. The method according to claim 30, wherein the composition comprises less than about 3 g of simple sugars other than fructose per serving or unit.

55. The method according to claim 30, wherein the composition comprises a simple sugar selected from the group consisting of sucrose, lactose and galactose.

56. The method according to claim 30, wherein the composition is substantially free of simple sugars.

57. The method according to claim 30, wherein the composition comprises about 3–20 g of protein per serving or unit.

58. The method according to claim 30, wherein the composition comprises about 2–7 g of fat per serving or unit.

59. The method according to claim 30, wherein the composition is in the form of a snack bar, pudding, cookie, wafer, or milkshake.

60. The method according to claim 30, wherein about 1–2 servings or units of the composition are administered to the patient.

61. The method according to claim 30, wherein about one-half serving or unit of the composition are administered to the patient.

* * * * *